(12) United States Patent
High et al.

(10) Patent No.: US 11,807,865 B2
(45) Date of Patent: Nov. 7, 2023

(54) LARGE COMMERCIAL SCALE LENTIVIRAL VECTOR PRODUCTION SYSTEM AND VECTORS PRODUCED THEREBY

(71) Applicant: The Children's Hospital of Philadelphia, Philadelphia, PA (US)

(72) Inventors: Katherine A. High, Merion Station, PA (US); John Fraser Wright, Princeton, NJ (US); Bernd Hauck, Hamilton, NJ (US); Guang Qu, Sicklervile, NJ (US)

(73) Assignee: The Children's Hospital of Philadelphia, Philadelphia, CA (US)

( * ) Notice: Subject to any disclaimer, the term of this patent is extended or adjusted under 35 U.S.C. 154(b) by 468 days.

(21) Appl. No.: 16/113,908

(22) Filed: Aug. 27, 2018

(65) Prior Publication Data

US 2019/0093126 A1    Mar. 28, 2019

Related U.S. Application Data

(63) Continuation of application No. 14/364,623, filed as application No. PCT/US2012/069212 on Dec. 12, 2012, now abandoned.

(60) Provisional application No. 61/569,765, filed on Dec. 12, 2011.

(51) Int. Cl.

| C12N 15/867 | (2006.01) |
|---|---|
| C12N 7/00 | (2006.01) |
| C12N 7/01 | (2006.01) |
| C12N 7/02 | (2006.01) |
| C12N 15/113 | (2010.01) |
| C12N 15/86 | (2006.01) |
| A61K 48/00 | (2006.01) |

(52) U.S. Cl.
CPC .............. *C12N 15/86* (2013.01); *C12N 7/00* (2013.01); *A61K 48/00* (2013.01); *C12N 2740/15041* (2013.01); *C12N 2740/15051* (2013.01); *C12N 2740/15052* (2013.01); *C12N 2740/16041* (2013.01); *C12N 2740/16051* (2013.01); *C12N 2740/16052* (2013.01); *C12N 2800/50* (2013.01)

(58) Field of Classification Search
None
See application file for complete search history.

(56) References Cited

U.S. PATENT DOCUMENTS

| 6,171,591 B1 | 1/2001 | Hall |
| 2002/0183247 A1 | 12/2002 | Doms |
| 2006/0234273 A1* | 10/2006 | Desprez ........... G01N 33/57492 435/6.12 |
| 2006/0257366 A1 | 11/2006 | Trono |
| 2008/0254008 A1 | 10/2008 | Dropulic et al. |
| 2009/0075383 A1* | 3/2009 | Buschmann ......... A61K 31/715 435/455 |
| 2009/0217399 A1 | 8/2009 | Stern et al. |
| 2010/0041141 A1 | 2/2010 | Trono |
| 2010/0173928 A1* | 7/2010 | Sabatini ............... G01N 33/573 514/291 |
| 2012/0190046 A1* | 7/2012 | Datta ................... G01N 33/574 435/7.9 |
| 2012/0328617 A1* | 12/2012 | Kang ...................... A61P 17/06 424/135.1 |
| 2016/0353521 A1* | 12/2016 | Reynolds ............. H05B 1/0261 |
| 2019/0085325 A1* | 3/2019 | Elling .................... C12N 15/11 |
| 2020/0309779 A1* | 10/2020 | Kim ..................... G01N 33/574 |

FOREIGN PATENT DOCUMENTS

| WO | 200066759 A1 | 11/2000 |
| WO | 2005118792 A1 | 12/2005 |
| WO | 2009153563 A1 | 12/2009 |
| WO | 2011007193 A1 | 1/2011 |
| WO | 2011097447 A2 | 8/2011 |

OTHER PUBLICATIONS

Miller et al, A rapid and efficient method for concentration of small volumes of retroviral supernatant, Nucleic Acids Research, 1996, vol. 24, No. 8 pp. 1576-1577.*
FIVEphoton Biochemicals, Calcium Phosphate Transfection Kits, 2009, pp. 1-4.*
Hauber et al, Improving Lentiviral Transduction of CD34+ Hematopoietic Stem and Progenitor Cells, Human Gene Therapy Methods, 2018 published online Jun. 2017, pp. 104-113.*
Schauber et al, Lentiviral vectors pseudotyped with baculovirus gp64 efficiently transduce mouse cells in vivo and show tropism restriction against hematopoietic cell types in vitro, Gene Therapy (2004) 11, 266-275.*

(Continued)

*Primary Examiner* — Maria Marvich
(74) *Attorney, Agent, or Firm* — PILLSBURY WINTHROP SHAW PITTMAN LLP; Robert M. Bedgood

(57) ABSTRACT

In accordance with the present invention, a method for increasing the yield of rLV vector particles comprising a trans gene encoding a therapeutic protein or fragment thereof is disclosed. In one approach, cells are transfected with plasmids encoding the necessary components for rLV production using a calcium chloride transfection mix at pH 7.1 wherein the calcium chloride and plasmids form a complex which is added to the cells at a constant speed. The cells are then incubated for a suitable time period wherein virus particle media is collected at least twice during the incubation period and stored in a cold storage unit, thereby reducing virus inactivation.

18 Claims, 7 Drawing Sheets

(56) References Cited

OTHER PUBLICATIONS

Zhao et al, Automation of large scale transient protein expression in mammalian cells, Journal of Structural Biology, (2011) 209-215.*
Lentivirus and Retrovirus 101: basic biology, 2007, UT-Southwestern, pages.*
Vasconselos et al, Electrochemical Evidence of Surfactant Activity of the Hepes pH Buffer Which May Have Implications on Trace Metal Availability to Cultures in Vitro, Analytical Biochemistry 241, 248-253 (1996).*
Ansorge, S., et al., Development of a Scalable Process for High-Yield Lentiviral Vector Production by Transient Transfection of HEK293 Suspension Cultures, Journal of Gene Medicine, 2009, 11(10):868-876.
Flemington Lab, Calcium Phosphate Transfection Method, downloaded Feb. 22, 2018, pp. 1-2.
Geraerts, et al., Upscaling of lentiviral vector production by tangential flow filtration, J. Gene Med., 2005, 7:1299-1310.
Giry-Laterriere M., et al., Lentiviral Vectors, Methods in Molecular Biology, 2011, 737:183-209.
Grimm, et al., Robotic High-Throughput Assay for Isolating Apoptosis-Inducing Genes, Bio Techniques, 2002, 32(3):670-676.
Morling et al., "Enhanced Transduction Efficiency of Retroviral Vectors Coprecipitated With Calcium Phosphase," Gene Therapy, 1995, 2(7):504-508.
OZ Bioscience, Calcium Phosphate Transfection Kit, Jun. 16, 2009, pp. 1-9.
Sastry, et al, Evaluation of Plasmid DNA Removal from Lentiviral Vectors by Benzonase Treatment, Human Gene Therapy., 2004,15(2): 221-226.
Schweizer, M., et al., Large-Scale Production Means for the Manufacturing of Lentiviral Vectors, Current Gene Therapy, 2010, 10(6):474-486.
Van Der Loo, et al., Scale-up and manufacturing of clinical-grade self-inactivating c-retroviral vectors by transient transfection, Gene Therapy, 2012, 19:246-254; [online publication Jul. 14, 2011].
Tiscornia, G., et al., Production and Purification of Lentiviral Vectors, 2006, Nature Protocols, 1(1):241-245.
Vasconcelos, et al., Electrochemical Evidence of Surfactant Activity of the Hepes pH Buffer Which May Have Implications on Trace Metal Availability to Cultures in Vitro, Analytical Biochemistry, 1996, 241:248-253.
G-Biosciences | The Protein Man's Blog | A Discussion of Protein Research, Detergents: Ionic, Non-Ionic, and Zwitterionic. What's the Difference? Posted by the the Protein Man on Feb. 8, 2017 2:05:00 PM.
"HEPES (4-(2-hydroxyethyl)-1-piperazineethanesulfonic acid)" from Wikipedia, the free encyclopedia. Last edit Jul. 31, 2022, 9:52 (UTC).

* cited by examiner

Flow Diagram for recombinant Lenti Vector (rLV) Manufacturing

1) Expand HEK293T Cells starting from a Qualified Cell Bank
   ↓
2) Seed HEK293T cells in cell factories
   ↓
3) Transfect HEK293T cells for rLenti generation
   ↓
4) Harvest (2) and clarification of the Supernatant Containing rLV Vector
   ↓
5) Tangential flow filtration and Nuclease treatment of harvest supernatants
   ↓
6) Pellet rLV by centrifugation, and re-suspend
   ↓
7) Concentrate rLV by centrifugation, and re-suspend
   ↓
8) Package and Store Final Product
   ↓
9) Complete Quality Control Testing
   ↓
10) Perform final Quality Assurance Review and Lot Release

Figure 3

LARGE COMMERCIAL SCALE LENTIVIRAL VECTOR PRODUCTION SYSTEM AND VECTORS PRODUCED THEREBY

This application is a continuation application of U.S. application Ser. No. 14/364,623, filed Jun. 11, 2014, now abandoned, which is the 371 filing of PCT/US2012/069212, filed Dec. 12, 2012, which claims the benefit of priority to U.S. Provisional Application No. 61/569,765, filed Dec. 12, 2011, the entire contents being incorporated herein by reference as though set forth in full.

FIELD OF THE INVENTION

This invention relates to the fields of molecular biology and gene therapy. More specifically, the invention provides improved processes for large scale production of lentiviral vectors comprising transgenes which encode medically beneficial products for clinical use.

BACKGROUND OF THE INVENTION

Several publications and patent documents are cited throughout the specification in order to describe the state of the art to which this invention pertains. Each of these citations is incorporated herein by reference as though set forth in full.

Viruses are biological agents that efficiently introduce their genetic material in a target cell upon infection and depend on the host cell for their replication. Vectors harbor genes of interest in place of the wild-type viral genes from which they are derived. Hence, non replicating vectors lack the genetic information for self-propagation in cells but retain the capacity for introducing genes of interest into the target cells. Lentiviral vectors (LV) are derived from viruses belonging to the retrovirus family (Retroviridae, genus lentivirus). LV provide one of the most practical gene transfer vehicles, both for research and gene therapy applications because of their stable integration in dividing as well as non-dividing cells and long-term transgene expression. Human immunodeficiency virus type I (HIV-I) is probably the best studied lentivirus, and despite its well-known human pathogenicity, it rapidly became apparent that HIV-derived vectors offered unique gene therapy solutions for differentiated and non-dividing cells. (Pauwells et al., (2009) Current Gene Therapy 9:459-474).

Recombinant Lentivirus (rLV) vectors have been employed as gene therapy vectors with recent success in the treatment of cancer, indicating that a very large number of persons, i.e. those with cancer, may benefit from rLV gene therapy. A critical and outstanding challenge in rLV manufacturing at this time is the need for high concentrations, typically >$3\times10^8$/mL, as well as large volumes of such high concentration vector to be able to effectively treat the numerous persons who may potentially benefit from gene therapy using these vectors. Key challenges to obtaining such quantities of rLV are to generate sufficient amounts of rLV during cell culture ('upstream') manufacturing, and to purify and concentrate with high yield the rLV so generated in cell culture, without loss or inactivation of the vector, which is unstable and readily inactivated. rLV is typically produced from cells cultured in multilayer cell factories and secreted into the cell culture medium. Standard 'crude' titers of rLV in the medium after cell culture performed to generate rLV are in the range $1\times10^5$ to $1\times10^6$ transducing units (TU)/mL. Crude titer targets using optimized methods are in the range, $1\times10^6$ to $1\times10^7$ TU/mL. rLV is an enveloped virus and is therefore extremely fragile and easily inactivated, therefore a fast purification method with low impact and sheer is desirable.

SUMMARY OF THE INVENTION

In accordance with the present invention, a method for increasing the yield of rLV vector particles comprising a transgene encoding a therapeutic protein or fragment thereof is disclosed. In one approach, cells are transfected with plasmids encoding the necessary components for rLV production using a calcium chloride transfection mix at pH 7.1 wherein the calcium chloride and plasmids form a complex which is added to the cells at a constant speed. The cells are then incubated for a suitable time period wherein virus particle media is collected at least twice during the incubation period and stored in a cold storage unit, thereby reducing virus inactivation. Viral particles are then concentrated via trangential flow filtration, followed by exposure to an enzyme which is effective to reduce nucleic acid contamination. The particles so treated are then pelleted by centrifugation, resuspended using solution containing a surfactant to improve the efficiency and yield for the resuspension steps. The resulting solution is then layered over an appropriate gradient and further centrifuged thereby further concentrating rLV at increased yield when compared to methods omitting these steps. In a preferred embodiment, recombinant LV particles are produced at approximately $3\times10^8$/ml. Also encompassed by the present invention is a rLV vector formulation comprising rLV particles purified using the method described above in a pharmaceutically acceptable carrier.

In one embodiment, the method is used to produce a rLV comprising a transgene encoding a nucleic acid selected from the group consisting of a siRNA, an antisense molecule, and a miRNA a ribozyme and a shRNA. In another embodiment the method is employed to produce a therapeutic gene product including but not limited to a protein, hormone, growth factor, receptor or antibody or fragment thereof. In a preferred embodiment, the gene product is Factor VIII or Factor IX.

BRIEF DESCRIPTION OF THE DRAWINGS

FIG. 3 is a flow chart showing steps used to obtain highly purified and highly concentrated infectious rLV.

DETAILED DESCRIPTION OF THE INVENTION

Figure 1:
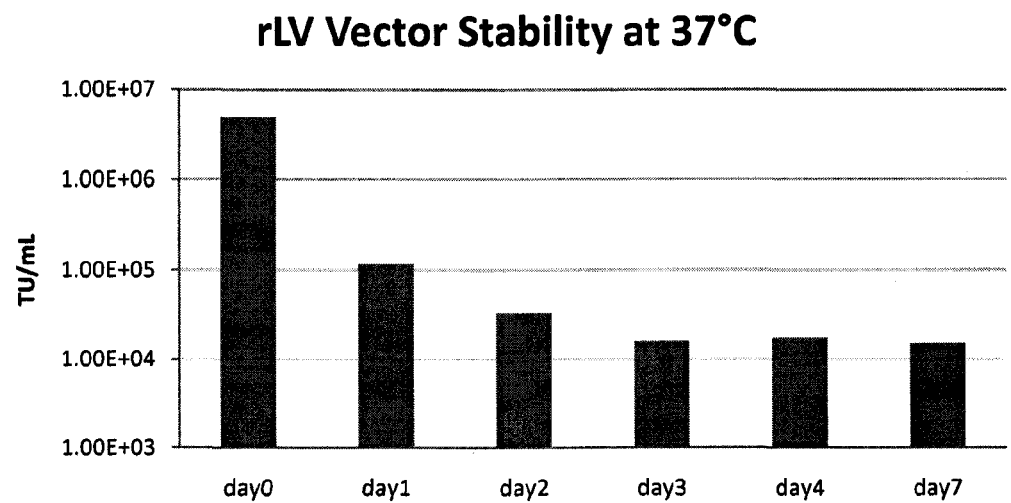
FIG. 1 is a graph showing rLV vector stability at 37° C. This data demonstrates that recombinant lentivirus vectors are rapidly inactivated at the temperature used for its generation in cell culture, and therefore carefully optimized timing of harvest is needed for high yield recovery of active vector.

The current invention provides an rLV vector manufacturing method that includes several features that distinguish it from current 'industry-standard' scalable rLV vector purification processes. These include; improved reagents and techniques for more efficient transfection; an optimized harvest schedule to recover the rLV generated during cell culture, thereby minimizing the instability of the rLV so generated, and more efficient purification of rLV transduction units that minimizes inactivation of rLV during processing.

Optimization of rLV vector generation and purification methods ensures that the vector product can efficiently deliver its genetic payload to target cells, and minimizes the potential for activation of deleterious immune responses. Development of manufacturing processes to purify recombinant rLV as a product to treat human disease must achieve the following objectives: 1) consistent vector purity, potency and safety; 2) manufacturing process scalability; and 3) acceptable cost of manufacturing. Current 'industry standard' scalable rLV vector production and purification processes do not adequately achieve optimal titers of the viral vector.

The following definitions are provided to facilitate the practice of the present invention.

Lentiviruses include members of the bovine lentivirus group, equine lentivirus group, feline lentivirus group, ovinecaprine lentivirus group and primate lentivirus group. The development of lentiviral vectors for gene therapy has been reviewed in Klimatcheva et al., 1999, Frontiers in Bioscience 4: 481-496. The design and use of lentiviral vectors suitable for gene therapy is described, for example, in U.S. Pat. No. 6,207,455, issued Mar. 27, 2001, and U.S. Pat. No. 6,165,782, issued Dec. 26, 2000. Additional systems are disclosed in Merten et al. (2011). Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus.

The terms "gag polyprotein", "pol polyprotein", and "env polyprotein" refer to the multiple proteins encoded by retroviral gag, pol and env genes which are typically expressed as a single precursor "polyprotein". For example, HIV gag encodes, among other proteins, p17, p24, p9 and p6. HIV pol encodes, among other proteins, protease (PR), reverse transcriptase (RT) and integrase (IN). HIV env encodes, among other proteins, Vpu, gp120 and gp41. As used herein, the term "polyprotein" shall include all or any portion of gag, pol and env polyproteins.

The terms "Vpx" and "Vpr" refer respectively to lentiviral Vpx and Vpr proteins described, for example, in WO 96/07741, hereby incorporated by reference in its entirety. These terms also refer to fragments, mutants, homologs and variants of Vpr and Vpx which retain the ability to associate with p6.

The term "fusion protein" refers to a molecule comprising two or more proteins linked together. Typically, the fusion protein is an amino acid sequence comprising two or more protein sequences.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "recombinant virus" is meant a virus that has been genetically altered, e.g., by the addition or insertion of a heterologous nucleic acid construct into the particle.

By "rLV virion" is meant a complete virus particle, such as a wild-type (wt) rLV virus particle (comprising a linear, double-stranded LV nucleic acid genome associated with an rLV envelope.

The terms "recombinant rLV virion," "rLV vector particle," and "full particles" are defined herein as an infectious, replication-defective virus including an rLV membrane envelope, and a transgene comprising a heterologous nucleotide sequence of interest. A review describing rLV molecular features is provided in Dropulic (2011).

The term "host cell" denotes, for example, microorganisms, yeast cells, insect cells, and mammalian cells, that can be, or have been, used as recipients of an rLV helper construct, an rLV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil-, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, Buracil-5-oxyacetic acid methylester, uracil-5-oxyacetic acid, pseudouracil, queosine, 2-thiocytosine, and 2,6-diaminopurine.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters."

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The transgene comprising the heterologous nucleic acid can encode a number of useful products. These can include siRNA, antisense molecules, and miRNAs for example. Alternatively, transgenes can encode hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor a (TGFa), platelet-derived growth factor (PDGF), insulin growth factors I and II (IGF-I and IGF-II), any one of the transforming growth factor 13 superfamily, including TGFß, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-I through IL-17, monocyte chemoattractant protein, leukemia inhibitory factor, granulocyte-macrophage colony stimulating factor, Fas ligand, tumor necrosis factors a and ß, interferons a, ß and γ; stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors single chain T cell receptors (e.g. Kalos et al 2011; Porter et al 2011), class I and class II MHC molecules, as well as engineered immunoglobulins and MHC molecules. Useful gene products also include regulatory proteins such as complement regulatory proteins, membrane cofactor protein (MCP), decay accelerating factor (DAF), CR1, CF2 and CD59.

Other useful gene products include those that can correct in born errors of metabolism. Such transgenes can encode for example, carbamoyl synthetase I, omithine transcarbamylase, arginosuccinate synthetase, arginosuccinate lyase, arginase, fumarylacetacetate hydrolase, phenylalanine hydroxylase, alpha-I antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Clinically useful lentiviral vectors may also express an antisense gene directed against the human immunodeficiency virus (HIV) (Levine et al 2006) and other important human pathogens.

These and other useful applications of rLV and related vectors have been recently reviewed and cited by Naldini (2011).

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

The present invention involves increasing rLV titers during large scale production and reducing, or eliminating, rLV vector related impurities (e.g. rLV associated nucleic acid impurities) contained within purified stocks of rLV virions, with minimal loss to rLV vector particles contained therein.

There are several methods that are well known in the art for generating rLV virions: for example, transfection using vector and rLV helper sequences. See for example, Merten et al 2011.

Purification of rLV Virions

Following recombinant LV replication (i.e. vector generation in cell culture systems), rLV virions can be purified from the host cell using a variety of conventional purification methods, such as column chromatography, sucrose gradient purification, and the like. For example, a plurality of column purification steps can be used, such as purification over DEAE chromatography resin (Merten et al 2011).

Recombinant LV vectors containing any number of reporter genes can be used to determine infectious titers. For example, alkaline phosphatase, beta-galactosidase (LacZ), green fluorescent protein, or luciferase may be used. Other assays use the therapeutic transgene nucleic acid, or transgene product as a target for the assay. An important factor is the cell line that is used for the test, since some cells are more susceptible to rLV than others. The obtained titer depends on the system and can largely differ when different assays are used.

For clinical applications requiring higher doses of vector, purified LV particles containing >50% LV vectors can be concentrated to $10^8$ particles per mL by tangential flow filtration (TFF) and centrifugation steps performed in a manner that minimizes the inactivation of the labile enveloped particles. For other clinical applications that require even greater doses of vector, purified LV particles containing >50% LV vectors can be concentrated to $10^9$ TU/mL by tangential flow filtration (TFF) and centrifugation steps performed in a manner that minimizes the inactivation of the labile enveloped particles.

For other clinical applications that require even greater doses of vector, purified LV particles containing >50% LV vectors can be concentrated to $10^{10}$ TU/mL, or greater, by tangential flow filtration (TFF) and centrifugation steps performed in a manner that minimizes the inactivation of the labile enveloped particles. Crude titers must be sufficiently higher to make the concentrations steps by tangential flow filtration and centrifugation steps reasonable and practical. Therefore achieving the highest possible crude titers is necessary to generate enough rLV during the cell culture process to be able to purify and concentrate sufficient rLV to make many human doses in a cost effective manner. For example, crude titers of $10^6$ TU/mL, more preferable $10^7$ TU/mL, and most preferably $10^8$ TU/mL and higher are required.

To test for infectious titer, the methods include the seeding of about 20,000 host cells per well, (preferably of human origin, most preferably SupT1 cells), into tissue culture-treated plates (e.g., 96-well plates). The virus is serially diluted and added to the cells and incubated for 3 days. On the third day, the cells are harvested and stained with antibodies against the transgene product. The cells are analyzed via FACS and the transduction titer (TU/mL) is calculated based on the dilution were transgene expression could be detected at a significant level.

The cell culture and purification method described herein provides vectors with an improved safety profile via efficient removal of vector related impurities in a manner that is scalable, i.e. preparation of large amounts of LV vectors in a cost effective manner is now possible. The process steps used for the cell culture and purification methods are summarized in the flow chart shown in FIG. 3, and described in additional detail below:

1) Step 1: Expansion of HEK293T Cells from a MCB

In one approach, 293T cells from a Master Cells Bank (MCB) or Working Cell Bank (WCB) prepared and qualified for use in current Good Manufacturing Practices (cGMP) manufacturing used for production (vector generation) are expanded in DMEM supplemented with 5% FBS, although other cell lines can be used for this purpose. Generally, one vial from the cell bank is expanded into a single T75 flask. Once confluent, the cells are then trypsinized, and replated first into 2×T175 flasks, then 5×T175 flasks, then to 2×4-layer cell factories (CF4), and ultimately into the full scale of the vector run (4 to 8 4-layer cell factories). Non-transfected cells are passaged in T175 and maintained flasks in a separate incubator to serve as starting material for additional rounds of cell factory seeding.

2) Step 2: Transfecting HEK293T Cells for rLV Vector Generation 293T cells are transfected once the cells reach >70% confluence. Transfection is performed using the calcium phosphate method. One component of the transfection buffer, 2×HEPES buffer solution is aliquoted into a number of separate storage bottles with enough buffer solution for a single cell factory unit. A second bottle is prepared containing calcium chloride, WFI-quality water and each of the four plasmid DNA solutions with enough volume for all of the CF units to be transfected. An equal volume of the calcium-DNA solution is mixed into the 2×HEPES solution bottle by pipette. The mixture is allowed to sit for ten minutes and then is poured into a bottle containing warmed cell culture media. Each CF is then emptied and replaced with ~0.4 L of the final transfection media. After approximately 6 hours, the transfection media is exchanged for regular media.

3) Step 3: Harvesting & Clarifying the rLV Supernatant and Harvesting EOP Cells

Vector is harvested at 48 and 72 hours after exchange of transfection media. Supernatant collected at 48 hours is stored at 4° C. overnight. Supernatant is collected at 72 hours. The 48 hour supernatant harvest is combined and collected with the 72 hour harvest and samples subjected to bioburden testing, titer determination and p24 analysis. The combined harvest pool is clarified through a 0.8 um over 0.45 um cartridge filter (Sartorius) with a flow rate of 400 mL/min into a new sterile bioprocess bag. Samples for bioburden testing, titer and p24 analysis are taken and the material is further processed immediately.

The End Of Production (EOP) cells in the cell factories are trypsinized, collected and counted. If the viability is >65%, 4 vials with $1 \times 10^7$ cells are frozen in liquid nitrogen for subsequent QC testing. The remainders of the cells are aliquoted and stored at <−60° C. In the case the EOP cells show a viability <65% the cells are cultured in T175 flasks and cryo preserved approximately 3 days later.

4) Step 4: Tangential Flow Filtration (TFF) & Benzonase Treatment of the rLV Supernatant The clarified supernatant harvest pool is concentrated through a hollow fiber cartridge filter with a 100000 MWCO (GE Healthcare) that is sanitized with 1N NaOH after initial set up and immediately after each use. The cartridge is equilibrated with sterile PBS and a neutral pH is verified. Connections are made in a class 100 BSC. The clarified harvest pool is added to the system and the volume is reduced ~6 fold. The concentrated harvest is recovered into a sterile bioprocess bag and then treated with benzonase (EMD, 300 U mL) for one hour at room temperature. Samples for bioburden testing, titer and p24 analysis are taken and the material is further processed immediately.

5) Step 5: Pelleting rLV Particles by Centrifugation

The concentrated benzonase-treated material is transferred to 6-8 250 ml conical centrifuge bottles and centrifuged at 4° C. for >18 hours at 38000×g (Avanti J-26XPI, Beckman). 10 mL of resuspension buffer is used per centrifuge bottle. The pellet containing the rLV is recovered and the rLV is extracted by up and down pipetting of the suspension. Large debris is pelleted by centrifugation at 3000 rpm and the supernatant containing the rLV is transferred to sterile 50 mL conical tubes. Samples for, titer and p24 analysis are taken and the material is further processed immediately.

6) Step 6: Sucrose Gradient Centrifugation and Storage of rLV

The vector suspension produced in MPR LXP102 is layered over 20% Sucrose Solution in 1×HBSS, pH 7.15 in sterile Oak Ridge Type Tubes. The material is centrifuged at 10° C. for >2 hours at 75000×g (Avanti J-26XPI, Beckman). The pellet containing vector is recovered from the centrifuge tubes and the rLV is extracted using Vector Storage Buffer. Samples for bioburden testing, titer and p24 analysis are taken. The resulting vector solution is stored in a conical tube at <−600 C.

7) Step 7: Packaging and Storage of Concentrated rLV

Following completion of the final manufacturing cycle all of the weekly production batches will be pooled, and in a class 100 BSC 1 mL is aseptically filled into 1.5 mL cryovials (Nalgene 5000-1020). The vials with rLV vector product are stored <−60° C.

The following examples are provided to illustrate certain embodiments of the invention. They are not intended to limit the invention in any way.

For the production (also known as generation), of rLV, HEK293T cells are transfected with plasmids encoding all the necessary information for rLV generation (Kalos et al, 2011; Porter et al, 2011), which is subsequently secreted into the cell culture medium supernatant.

Figure 2:
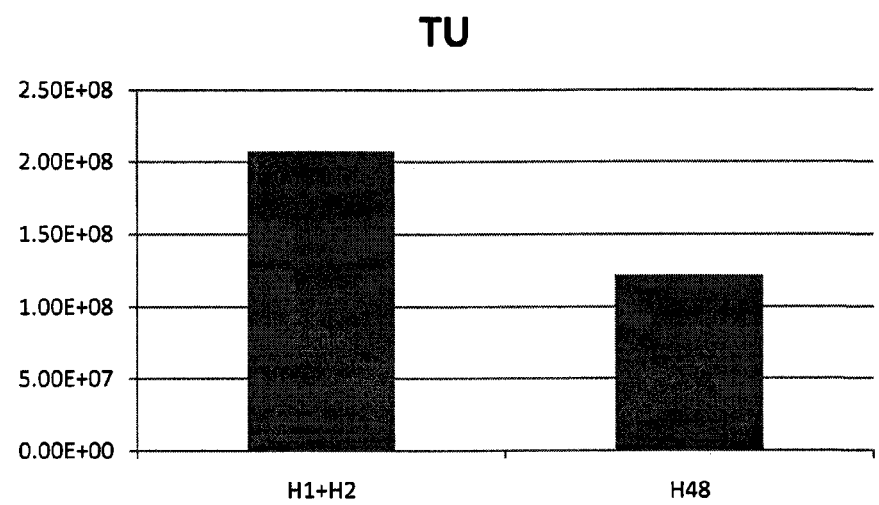
FIG. 2 is a graph showing the amount of transduction units produced in the first 48 hours.
Figure 4A:
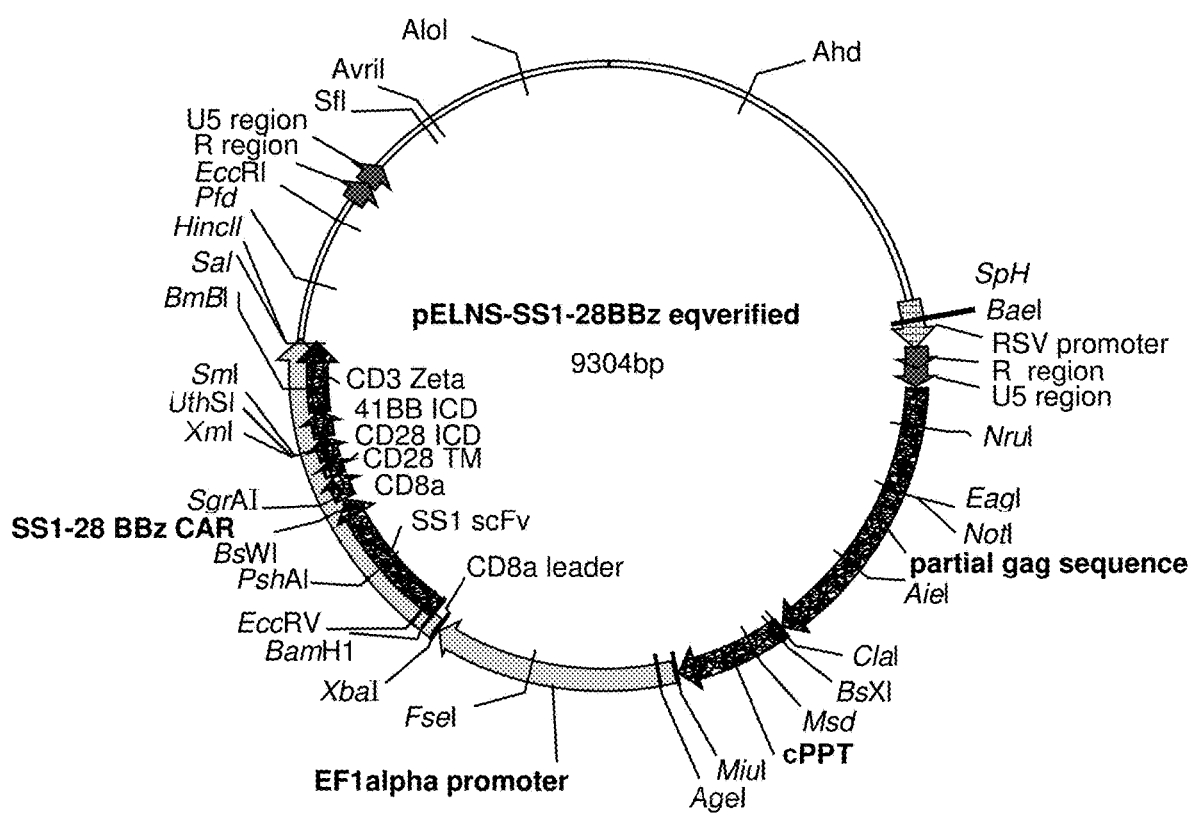
FIGS. 4A-4D show maps for plasmids used for rLV manufacturing, however many different alternatives are available to the skilled artisan. These plasmids were used in the manufacture of rLV lots using transient transfection of HEK293T cells.
Figure 4B:
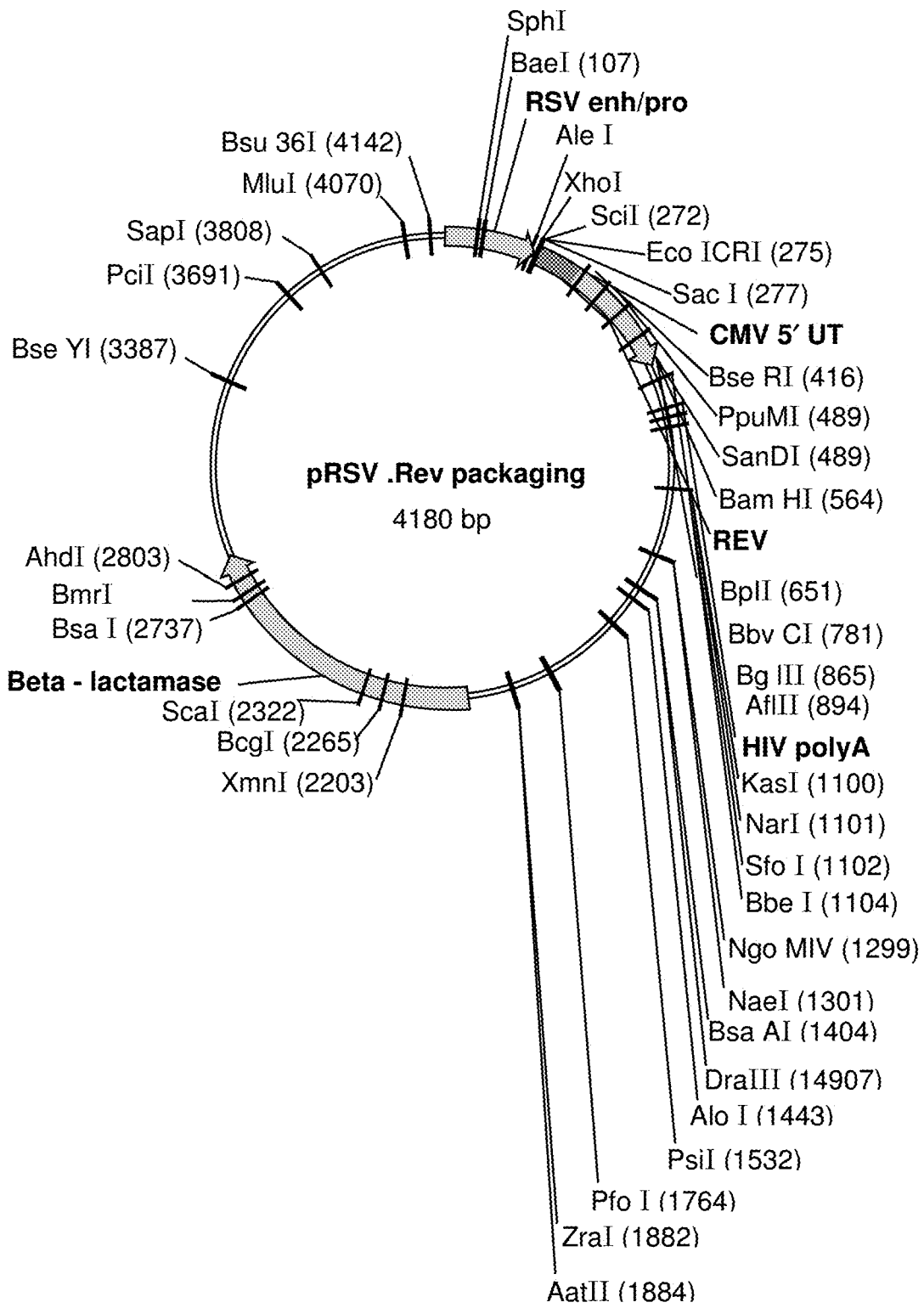
Figure 4C:
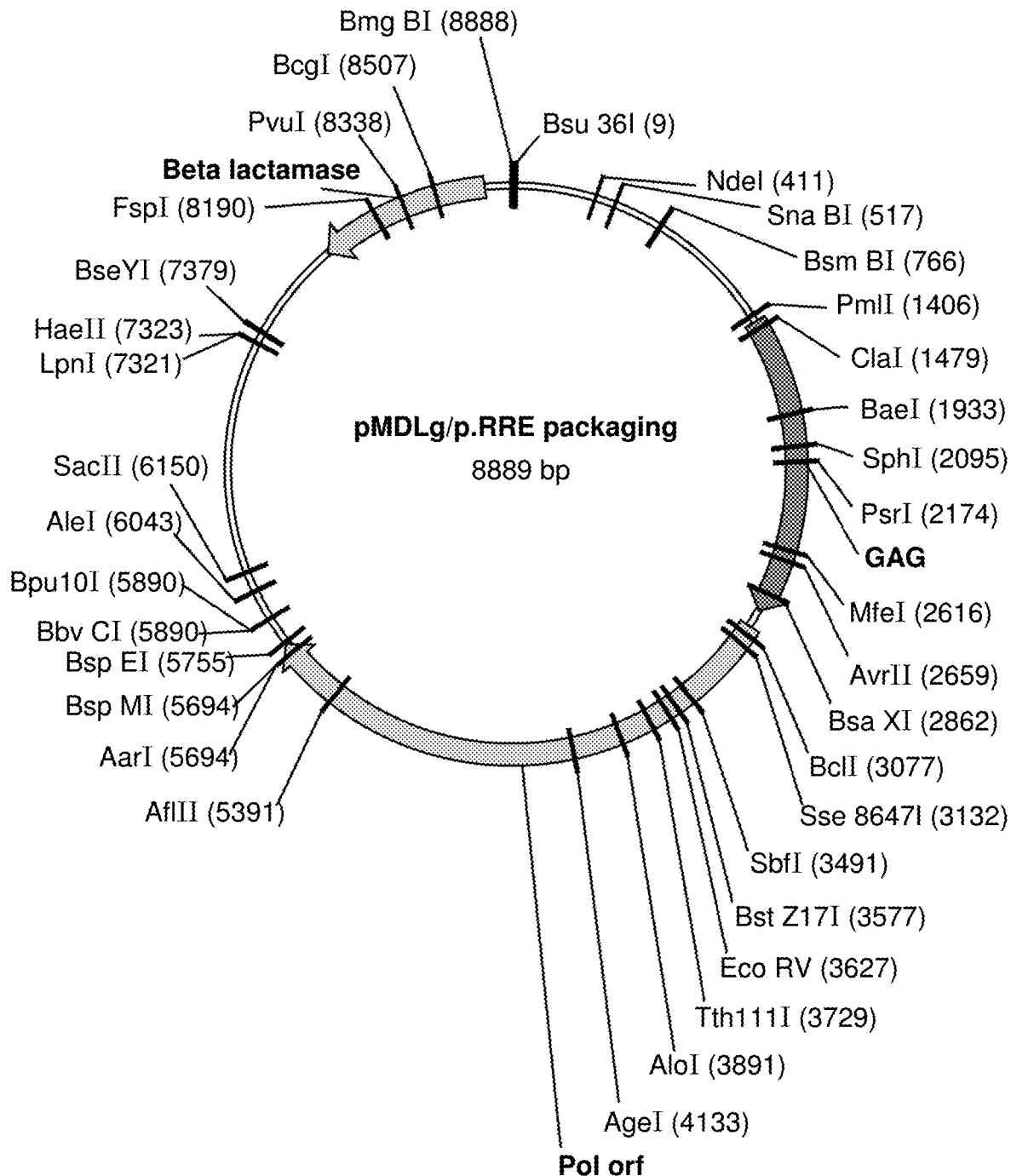
Figure 4D:
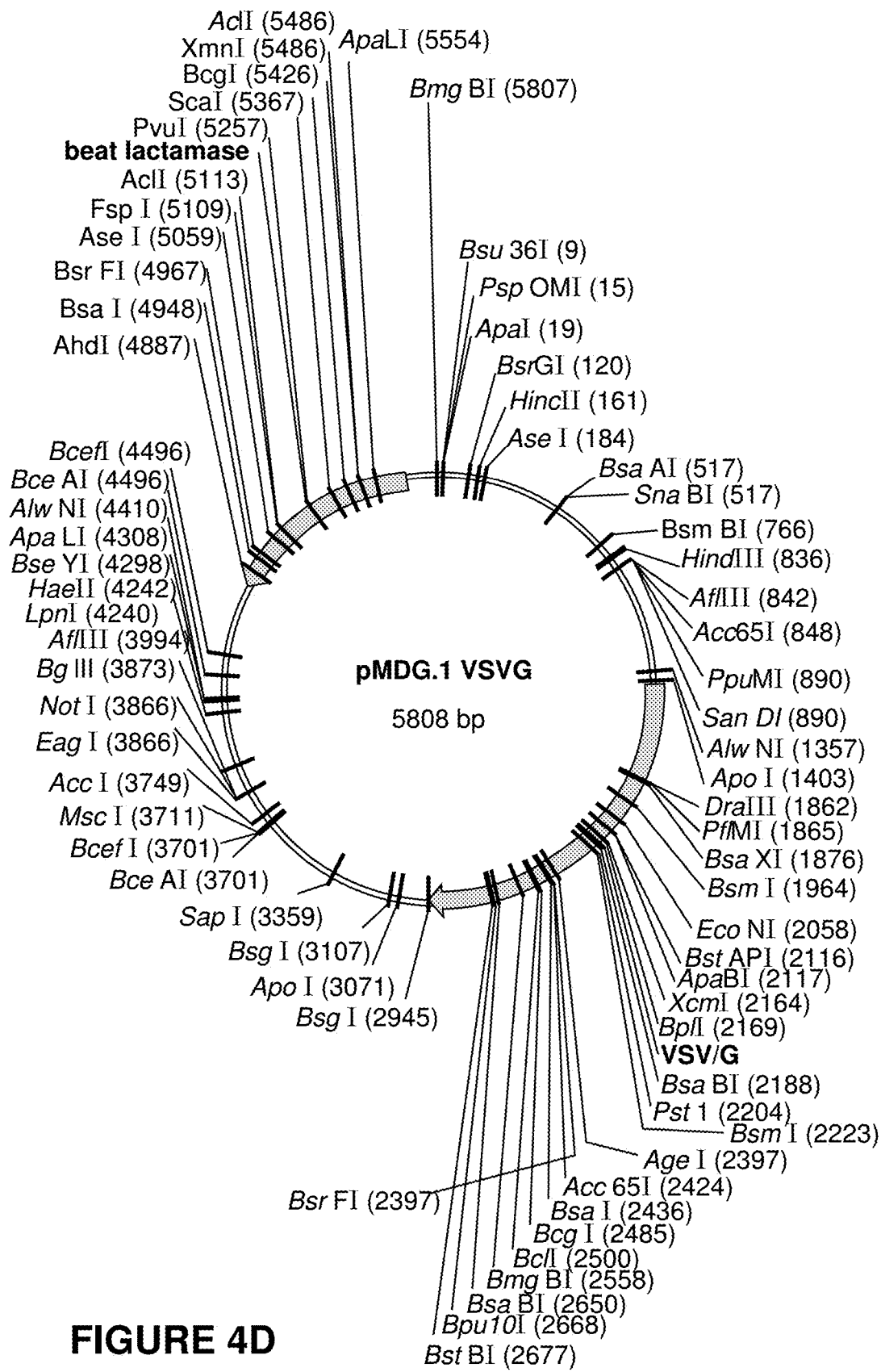

After transfection, the cell culture medium is collected to recover the rLV. The methods to generate rLV using plasmid transfection are known in the field. The present invention provides methods which give rise to improved and efficient generation and recovery of rLV to meet the requirements for large scale human gene therapy trials. The industry established harvest schedule is typically 48 and 72 hours post transfection. rLV is an enveloped virus which is not very stable at high temperatures (FIG. 1). We have found that early transfer of rLV containing medium into a cold storage unit early, e.g., within 56 hours, increases the amount of active vector particles as measured in Transduction Units (TU). In the standard harvest schedule, cells are incubated with medium at 37° C. for 48 hours until the medium is harvested. If the medium is harvested earlier, at 32 hours and transferred to cold storage, the incubation time at 37° C. and therefore LV inactivation is reduced. FIG. 2 shows that more active TUs are recovered when the incubation time is split, meaning two harvests (H1 at 32 hours and H2 at 48) compared to the single harvest incubating at 37° C. for 48 hours (H48). While 32 and 48 hours are shown here, culture time can be expanded out the 52, 56 and 60 hours for example.

The preparation of the transfection mixture is a crucial step for rLV production since rLV generation correlates to the efficacy of transfection. In this process, a solution containing DNA (FIG. 4) and 1.25M Calcium Chloride (CaCb) is added to a 2×HEBS buffer containing 282 mM Sodium chloride/1.48 mM Sodium phosphate dibasic/50 mM HEPES, upon contact the DNA-$CaCl_2$ complex is precipitated, forming the active reagent for transfection. Controlling the speed of addition and the mixing of the solutions is a critical parameter. In the industry standard setting the DNA-$CaCl_2$ solution is added manually using a pipette aid and the solutions are mixed by hand. This does not allow for an objective control of the speed and is highly variable between operators. In addition, this procedure does not allow the preparation of large volumes, so transfection mixes have to be prepared individually for each cell culture unit adding another factor of variability. We have changed the preparation of the transfection mix by using the same 2×HEBS buffer at a higher pH, 7.1, lowering the $CaCl_2$ concentration to 0.75M, adding the DNA-$CaCl_2$ solution at a constant speed (200 mL/min), and preparing a larger volume of transfection mix sufficient for 4 cell culture units. This provides consistency between transfection batches and different operators. Table 1 shows the increased rLV production, measured in production per cell culture surface, of the improved method compared to the uncontrolled hand dripping method. The improved method leads to a 10× increase in rLV vector production.

The downstream purification process involves a concentration step using tangential Flow Filtration (TFF), Benzonase digestion (200 U/mL) to remove nucleic acid contamination, a centrifugation step to further concentrate the rLV (38,400 g for 18 hours), and a 20% Sucrose gradient centrifugation (75,600 g for 2 hours). It is crucial that the rLV purification minimizes inactivation of the rLV particles. Inactivation occurs through extensive exposure to temperatures above room temperature and mechanical sheer forces that destroy the lipid membrane envelope of the vector. Using a large scale TFF system (GE, FlexStand with a 100 kDa cut off cartridge UFP-100-C-9A and applying a Trans membrane pressure of 7 PSI) the process time for concentration is greatly reduced to around 30 minutes, compared to a few hours when previous process is used. The re-suspension of rLV from the pellets is traditionally performed using hand held serological pipettes. In this process uncontrollable air bubbles can be introduced and the re-suspension efficacy is limited. In the improved process a fixed volume pipette (Finn pipette F2, 0.2-5 mL, Thermo Scientific) is used eliminating the rLV inactivating air bubbles.

In addition a surfactant, Pluronic F68®, BASF, is added to the re-suspension buffer at a low concentration, 0.0001%, facilitating the release of the rLV particles from the pellets obtained.

The 10× increased productivity during the upstream cell culture process is carried over to the final purified vector where a 10× increase in productivity is achieved in the improved process, Table 2.

The changes in the upstream cell culture and downstream purification procedures lead to an increased (3-10 fold) rLV productivity resulting in vector preparations with increased titers needed for clinical applications.

TABLE 1

Amount of rLV particles in harvested media.

| | Standard transfection experiment #1 | Standard transfection experiment #2 | Modified transfection experiment #1 | Modified transfection experiment #2 |
|---|---|---|---|---|
| Total PP per 632 cm$^2$ | $1.38 \times 10^{11}$ | $2.72 \times 10^{11}$ | $9.2 \times 10^{11}$ | $7.13 \times 10^{11}$ |
| Total TU per 632 cm$^2$ | $1.34 \times 10^{9}$ | $3.16 \times 10^{8}$ | $3.4 \times 10^{9}$ | $3.06 \times 10^{9}$ |

TABLE 2

Amount of purified rLV particles.

| | Standard transfection experiment #1 | Standard transfection experiment #2 | Modified transfection experiment #1 |
|---|---|---|---|
| Total PP per 632 cm$^2$ | $5.64 \times 10^{10}$ | $2.81 \times 10^{10}$ | $1.56 \times 10^{11}$ |
| Total TU per 632 cm$^2$ | $6.88 \times 10^{7}$ | $9.06 \times 10^{7}$ | $6.59 \times 10^{8}$ |

REFERENCES

Kalos M, Levine B L, Porter D L, Katz S, Grupp S A, Bagg A, and June C H (2011). T cells with chimerical antigen receptors have potent antitumor effects and can establish memory in patients with advanced leukemia. Science Translational Medicine 3:1

Porter D L, Levine B L, Kalos M, Bagg A, June C H (2011). Chimeric antigen receptor-modified T cells in chronic Lymphoid leukemia. N Engl J Med 365:725.

Merten, O-W, Charrier S, et al (2011) Large-scale manufacture and characterization of a lentiviral vector produced for clinical ex vivo gene therapy application. Human Gene Therapy 22:343.

Levine B L, Humeau L M, et al (2006). Gene transfer inhumans using a conditionally replicating lentiviral vector. Proc Natl Acad Sci USA 103:17372.

Naldini L (2011). Ex vivo gene transfer and correction for cell-based therapies. Nature Reviews Genetics 12:301.

Dropulic B (2011). Lentiviral vectors: their molecular design, safety and use in laboratory and preclinical research. Human Gene Therapy 22:649.

While the invention has been described in detail and with reference to specific examples thereof, it will be apparent to one skilled in the art that various changes and modifications can be made therein without departing from the spirit and scope thereof.

What is claimed is:

1. A method for producing recombinant lentivirus (rLV) comprising a therapeutically beneficial transgene for clinical applications, the method comprising the steps:
   (a) transfecting host cells with a transfection mix, wherein plasmids and calcium chloride are mixed thereby forming said transfection mix, followed by adding said transfection mix at a controlled speed to said host cells in a media;
   (b) incubating the host cells transfected in step (a) in the media for a time period wherein the rLV particle is produced and thereafter the media comprising the rLV particle is collected only two times, and after the first collection, replacement media is added, during the time period up to 60 hours after transfection, and placing the collected rLV particle media in a storage unit;
   (c) concentrating the rLV particles in the collected media from step (b) via tangential flow filtration;
   (d) treating the concentrated rLV particles from step (c) with an enzyme which reduces nucleic acid contamination;
   (e) centrifuging the rLV particles treated in step (d) to further concentrate said rLV in a pellet and resuspending the centrifuged rLV pellet in a solution containing a surfactant to release said rLV; and
   (f) layering the rLV in the surfactant solution of step (e) over a sucrose gradient followed by further centrifuging, thereby producing the rLV for clinical applications.

2. The method according to claim 1, wherein said transgene comprises a nucleic acid selected from the group consisting of a siRNA, an antisense molecule, a miRNA, a ribozyme and a shRNA.

3. The method according to claim 1, wherein said transgene encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor alpha (TGFalpha), platelet-derived growth factor (PDGF), insulin growth factor I, insulin growth factor II, TGFbeta, activins, inhibins, bone morphogenic protein (BMP), nerve growth factor (NGF), brain-derived neurotrophic factor (BDNF), neurotrophin NT-3, neurotrophin NT4/5, ciliary neurotrophic factor (CNTF), glial cell line derived neurotrophic factor (GDNF), neurturin, agrin, netrin-1, netrin-2, hepatocyte growth factor (HGF), ephrins, noggin, sonic hedgehog and tyrosine hydroxylase.

4. The method according to claim 1, wherein said transgene encodes a gene product selected from the group consisting of thrombopoietin (TPO), an interleukin, an interleukin selected from the group consisting of IL-1, IL-2, IL-3, IL-4, IL-5, IL-6, IL-7, IL-8, IL-9, IL-10, IL-11, IL-12, IL-13, IL-14, IL-15, IL-16 and IL-17, monocyte chemoattractant protein, leukemia inhibitory factor, granulocyte-macrophage colony stimulating factor, a Fas ligand, tumor necrosis factor alpha, tumor necrosis factor beta, interferon alpha, interferon beta, interferon gamma, a stem cell factor, a flk-2/flt3 ligand, an IgG, an IgM, an IgA, an IgD, an IgE, a chimeric immunoglobulin, a humanized antibody, a single chain antibody, a T cell receptor, a chimeric T cell receptor, a single chain T cell receptor, a class I MHC molecule and a class II MHC molecule.

5. The method according to claim 1, wherein said transgene comprises a nucleic acid encoding a protein useful for correction of inborn errors of metabolism selected from the group consisting of carbamoyl synthetase I, ornithine transcarbamylase, argininosuccinate synthetase, argininosuccinate lyase, arginase, fumarylacetacetate hydrolase, phenylalanine hydroxylase, alpha-1 antitrypsin, glucose-6-phosphatase, porphobilinogen deaminase, Factor V, Factor VIII, Factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, RPE65, H-protein, T-protein, a cystic fibrosis transmembrane regulator (CFTR) sequence, and a dystrophin cDNA sequence.

6. The method according to claim 5, wherein the transgene comprises a nucleic acid encoding Factor VIII or Factor IX.

7. The method according to claim 1, wherein said transfection mix is at pH 7.1.

8. The method according to claim 1, further comprising recovering said rLV after centrifuging of step (f).

9. The method according to claim 8, further comprising resuspending the recovered rLV in a solution containing a surfactant.

10. The method according to claim 9, wherein said surfactant comprises Poloxamer 188.

11. The method according to claim 1, wherein the media comprising the rLV particle is collected at 32 hours after transfection, replaced with fresh media, and then collected at 48 hours after transfection.

12. The method according to claim 1, wherein the media comprising the rLV particle is collected at 32 hours after transfection, replaced with fresh media, and then collected at 52, 56 or 60 hours after transfection.

13. The method according to claim 1, wherein said rLV produced in step (f) is resuspended to at least $3 \times 10^8$ transduction units (TU)/ml.

14. The method according to claim 1, wherein said rLV produced in step (f) is resuspended to approximately $1 \times 10^8$ TU/ml or higher.

15. The method according to claim 1, wherein said rLV produced in step (f) is resuspended to approximately $1 \times 10^9$ TU/ml.

16. The method according to claim 1, wherein said rLV produced in step (f) is resuspended to approximately $1 \times 10^{10}$ TU/ml or greater.

17. The method according to claim 1, wherein said host cells are yeast cells, insect cells, or mammalian cells.

18. The method according to claim 1, wherein said host cells are HEK 293T cells.

* * * * *